(12) United States Patent
Weinschenk et al.

(10) Patent No.: US 9,783,849 B2
(45) Date of Patent: Oct. 10, 2017

(54) METHOD FOR IDENTIFYING IMMUNOREACTIVE PEPTIDES

(71) Applicant: immatics biotechnologies GmbH, Tuebingen (DE)

(72) Inventors: Toni Weinschenk, Aichwald (DE); Hans Georg Rammensee, Tuebingen (DE)

(73) Assignee: immatics biotechnologies GmbH, Tuebingen (DE)

( * ) Notice: Subject to any disclaimer, the term of this patent is extended or adjusted under 35 U.S.C. 154(b) by 0 days.

(21) Appl. No.: 14/503,690

(22) Filed: Oct. 1, 2014

(65) Prior Publication Data

US 2015/0044246 A1 Feb. 12, 2015

Related U.S. Application Data

(63) Continuation of application No. 13/775,095, filed on Feb. 22, 2013, now abandoned, which is a continuation of application No. 11/000,474, filed on Nov. 29, 2004, now abandoned, which is a continuation of application No. PCT/EP03/05038, filed on May 14, 2003.

(30) Foreign Application Priority Data

May 29, 2002 (DE) .................................. 10225139

(51) Int. Cl.

| G01N 33/50 | (2006.01) |
|---|---|
| G01N 33/53 | (2006.01) |
| G01N 33/574 | (2006.01) |
| G01N 33/68 | (2006.01) |
| C07K 7/00 | (2006.01) |
| A61K 38/04 | (2006.01) |
| C12Q 1/68 | (2006.01) |
| C07K 14/47 | (2006.01) |
| A61K 39/00 | (2006.01) |

(52) U.S. Cl.
CPC ........ C12Q 1/6876 (2013.01); C07K 14/4748 (2013.01); C12Q 1/6837 (2013.01); G01N 33/57484 (2013.01); A61K 38/04 (2013.01); A61K 39/00 (2013.01); A61K 2039/55 (2013.01); A61K 2039/572 (2013.01); C07K 7/00 (2013.01); C12Q 2600/136 (2013.01); C12Q 2600/158 (2013.01); G01N 33/50 (2013.01); G01N 33/53 (2013.01); G01N 33/574 (2013.01); G01N 33/68 (2013.01)

(58) Field of Classification Search
None
See application file for complete search history.

(56) References Cited

U.S. PATENT DOCUMENTS

| 5,747,269 A | 5/1998 | Rammensee et al. | |
|---|---|---|---|
| 6,022,697 A | 2/2000 | Kaufman et al. | |
| 6,759,046 B1 * | 7/2004 | Gaudernack ....... | C07K 14/4748 424/184.1 |
| 7,105,162 B1 * | 9/2006 | Schmidt ............ | A61K 39/0011 424/185.1 |
| 2009/0162405 A1 * | 6/2009 | Qian .................. | A61K 39/0011 424/277.1 |

FOREIGN PATENT DOCUMENTS

| WO | 99/19349 | 4/1999 |
|---|---|---|
| WO | 00/52157 | 9/2000 |
| WO | 00/73438 | 12/2000 |
| WO | 01/11040 | 2/2001 |
| WO | 01/40271 | 6/2001 |
| WO | 03/102023 | 12/2003 |

OTHER PUBLICATIONS

Hoffmann et al., J. Immunol., 2000, 165:5938-5944.*
Luzzi et al., Am. J. Pathol., 2001, 158(6): 2005-2010.*
Japanese Office Action for Japanese Patent Application No. 2004-507838 dated September 9, 2008 (9 Pages).
Young et al.; Am. J. Pathol.; 2001; 158: 1639-1651.
Flad et al.; Cancer Res.; 1998; 58: 5803-5811.
Maecker et al.; Curr. Mol. Med.; 2001; 1: 609-619.
Guo et al.; Zhonghua Yi Xue Za Zhi; 2001; 81:30-32 (Abstract Only).
International Search Report for PCT/EP03/05038 dated April 15, 2004 (8 Pages).
Mathiassen et al.; Eur. J. Immunol.; 2001; 31:1239-1246.
Rae et al.; Int. J. Cancer; 2000; 88:726-732.
Renkvist et al.; Cancer Immunotherapy; 2001; 50:3-15.
Schirle et al; Eur. J. Immunol.; 2000; 30:2216-2225.
Schirle et al.; J. Immunol. Methods; 2001; 257:1-16 (Abstract).
Schultze and Vonderheide; Trends in Immunology; 2001; 22(9):516-523.
Weinschenk et al.; Cancer Research; 2002; 62:5818-5827.
Zhao et al.; J. Immun.; 2001; 167:2130-2141.
Celis et al., "Induction of Anti-Tumor Cytotoxic T Lymphocytes in Normal Humans Using Primary Cultures and Synthetic Peptide Pitopes", Proc. Natl. Acad. Sci. USA, vol. 91, pp. 2105-2109, Mar. 1994.
Van Der Bruggen et al., "A Gene Encoding an Antigen Recognized by Cytolytic T Lymphocytes on a Human Melanoma", Science, 1991, 254 (5038), p. 1643.
Cox et al., "Identification of a Peptide Recognized by Five Melanoma-Specific Human Cytotoxic T Cell Lines"Science, 1994, 264 (5159), p. 716.

(Continued)

Primary Examiner — Hong Sang
(74) Attorney, Agent, or Firm — McBee Moore Woodward & Vanik IP, LLC; Susan McBee (57) ABSTRACT

The invention relates to a method for identifying immunoreactive peptides. According to said method, a sample of tumorous and corresponding healthy tissue is first provided, the tumor-specific expression profile is subsequently determined and antigenic peptides are isolated from the tumorous tissue and analyzed. The respective data that has been obtained is then matched and peptides are identified on the basis of said data.

26 Claims, 2 Drawing Sheets

(56) References Cited

OTHER PUBLICATIONS

F. Hoffmann La Roche Ltd., "Roche and immatics sign cancer vaccine and immunotherapy collaboration", available at http://www.roche.com/research_and_development/partnering/partnering-media/partnering_news-2013-11-13.htm , Nov. 11, 2013.

* cited by examiner

METHOD FOR IDENTIFYING IMMUNOREACTIVE PEPTIDES

CROSS-REFERENCE TO RELATED APPLICATIONS

This application is a Continuation of U.S. application Ser. No. 13/775,095, filed Feb. 22, 2013 (now abandoned), which is a Continuation of U.S. application Ser. No. 11/000, 474, filed Nov. 29, 2004 (now abandoned), incorporated herein by reference in its entirety, which is a Continuation of International Application No. PCT/EP03/05038, filed May 14, 2003, designating the United States and published in German as WO 03/100432, which claims priority to German Application No. 102 25 139 0.8, filed May 29, 2002, the contents of which are incorporated herein by reference in their entireties.

TECHNICAL FIELD

The invention relates to a method for identifying and to a method for preparing immunoreactive peptides and to the immunoreactive peptides identified/prepared thereby.

Such peptides are being used—for example—in immunotherapy of tumor-associated diseases. When tumor cells are eliminated by the immune system the identification of tumor-associated antigens (TAA) by components of the immune system plays a pivotal role. This mechanism is based upon the fact that there exist qualitative or quantitative differences between tumor cells and normal cells. To induce an anti-tumor response, the tumor cells have to express antigens which induce an immune response being sufficient for the elimination of the tumor.

CD8 expressing cytotoxic T-lymphocytes (in the following CTL), in particular, are involved in rejection of tumors. To induce such an immune reaction by cytotoxic T-cells foreign proteins/peptides have to be presented to T-cells. Antigens are recognized as peptide fragments by T-cells only if they are presented by MHC-molecules on cell surfaces. These MHC ("major histocompatibility complex") molecules are peptide receptors which normally bind peptides intracellularly and transport them to the cell surface. This complex of peptide and MHC-molecule is recognized by T-cells. Human MHC-molecules are also designated as human leukocyte antigens (HLA).

In the past, antigen-specific immunotherapy based on T-cells has proven successful in the treatment of cancer.

Induction of a specific CTL response directed against a tumor is dependent on identification of MHC class I-ligands derived from tumor-associated antigens (TAA). Such TAA can be exclusively present in malignant cells, for example as products of mutated genes. Other important classes of tumor-associated antigens are tissue-specific structures such as the cancer-testis antigens, and a third class of tumor-associated antigens are proteins overexpressed in tumors.

BACKGROUND ART

The methods for identification and characterization of TAA, which represent the starting point for a tumor vaccine, are—on the one hand—based on the use of patient derived CTL or antibodies. This immunological approach is combined either with a gene expression approach or with a mass-spectrometry (MS)-assisted sequencing of the recognized peptides (see van der Bruggen, et al., 1991, A gene encoding an antigen recognized by cytolytic Tlymphocytes on a human melanoma, Science 254: 1643-1647, and Cox et al., 1994, Identification of a peptide recognized by five melanoma-specific human cytotoxic T-cell lines, Science 264: 716-719). Methods for identifying TAA which are based on comparative transcription profiling of tumorous and corresponding normal tissue are—for example—hybridization and the use of DNA microarray technology.

Celis et al., 1994, Induction of anti-tumor cytotoxic T-lymphocytes in normal humans using primary cultures and synthetic peptide epitopes, Proc. Natl. Acad. Sci. USA 91: 2105-2109, applied a method which takes advantage of the prediction of MHC class I-ligands derived from a selected tumor-associated antigen, and in which these ligands were verified as Tcell epitopes in a next step.

Drawbacks of patients-derived T-cell-based approaches are the extensive culture techniques and their restriction to the frequency of pre-existing T-cells.

Another T-cell-independent approach also known in the art combines epitope prediction and screening for predicted peptides in complex peptide mixtures, the peptides being identified by highly sensitive capillary liquid chromatography mass spectrometry (LC-MS) (see Schirle et al., 2000, Identification of tumor-associated MHC class I-ligands by a novel T-cell independent approach, Eur. J. Immunol. 30: 2216-2225).

DNA microarray technology provides a new approach using comparative expression profiling of tumorous and corresponding autologous normal tissue. Young et al., 2001, Expression profiling of renal epithelial neoplasms: a method for tumor classification and discovery of diagnostic molecular markers, Am. J. Pathol. 158: 1639-1651, disclosed that by using this technique a large number of tumor-associated antigens from individual tumor samples can be identified. MHC-I-ligands derived from overexpressed or selectively expressed proteins provide possible targets for specific CTL recognition of tumors. Mathiassen et al., 2001, Tumor-associated antigens identified by mRNA expression profiling induce protective antitumor immunity, Eur. J. Immuno. 31: 1239-1246, demonstrated, in a mouse model, that by combining expression analysis with epitope prediction a successful vaccine can be prepared.

However, a disadvantage is that epitope prediction even for only a few target genes results in the identification of a vast number of candidate peptides, the majority of which are actually not presented by MHC molecules and thus do not induce a CTL-response.

DISCLOSURE OF THE INVENTION

Therefore, it is an object of the present invention to provide a new method for selective and simple identification of immunoreactive peptides.

According to the invention, this object is achieved by means of a method for identifying immunoreactive peptides comprising:

(a) providing a sample of tumorous and corresponding healthy tissue;
(b) determining tumor-specific expression profile of the provided sample,
(c) isolating and analyzing of antigenic peptides in the sample of tumorous tissue,
(d) matching data obtained in step (b) and (c), and
(e) identifying peptides on basis of the matched data.

The inventors revealed that by combining an expression analysis with antigenic tumor peptides, which have been isolated and analyzed, specific candidates for an individual vaccine can be identified.

By isolating antigenic peptides and matching them with gene expression profiles of tumorous tissue it can be avoided that a vast number of possible immunoreactive peptides is obtained. Rather, specific peptides are identified, which are actually presented by MHC molecules and which are thus suitable as immunoreactive peptides.

With the method according to the invention it is, respectively, possible to identify patient-specific peptides, i.e. it is possible to precisely match peptides, which are to be used as vaccine, to the patient, in order to induce a specific immune response.

For example, industrial laboratories—after having received patient samples—can systematically and efficiently perform this method, and can—after having identified suitable immunoreactive peptides—provide clinics in charge with the peptide sequences; the clinics can then synthesize and administer the peptides. Nevertheless, it is also possible that a laboratory is carrying out identification as well as production of the peptides suitable for the respective patient.

Therefore, the new method is applicable within the scope of a mere service as well as in combination with the supply of the identified immunoreactive peptide.

A further object is the method according to the invention, wherein the peptides isolated in step (c) are MHC-ligands.

Only peptides which are bound to MHC-molecules can induce a cellular immune response. Peptides which are derived, for example, from overexpressed genes of a tumor but which are not bound to MHC-molecules, do not induce a CTL immune reaction. Therefore, not all peptides, for example, identified solely by epitope prediction are immunoreactive.

A further object is the method according to the invention, wherein step (b) is performed by means of a microarray-analysis and/or reverse transcription-polymerase chain reaction.

With microarray analysis the expression profile of tumorous tissue is compared with corresponding normal tissue by using certain DNA- or gene-chips, and selectively expressed or overexpressed genes are identified. This method is well known in the art and is, for example, disclosed in Schena et al., 1995, Quantitative monitoring of gene expression patterns with a complementary DNA microarray, Science 270: 467-470.

Reverse transcription-polymerase chain reaction (in the following RT-PCT) can be utilized to quantify expression of a gene.

For this purpose cDNA is generated from RNA, which—for example—has been isolated from tumor cells, and the cDNA is consequently used as template for PCR. In that way, on the basis of the amplified DNA one can compare which genes are being transcribed with which intensity.

Yet a further object is the method according to the invention, wherein step (c) is performed by means of a mass spectrometer.

Using this technique each peptide can be identified precisely and efficiently with high performance. For example, Schirle et al., 2000, Identification of tumor-associated MHC class I ligands by a novel T-cell-independent approach, Eur. J. Immunol. 30: 2216-2225, describe the use of mass spectrometry to identify peptides derived from tumor tissue.

A further object is the method according to the invention, wherein in step (c) candidate antigenic peptides are predicted on the basis of the expression profile using suitable databases, and the mass spectrometer is calibrated with respect to the predicted antigens.

Use of databases for prediction of candidate antigens and utilizing the obtained data is—for example—disclosed in Schirle et al., 2001, Combining computer algorithms with experimental approaches permits rapid and accurate identification of T-cell epitopes from defined antigens, J. Immunol. Methods, 257: 1-16.

Yet a further object is the method according to the invention, wherein step (c) is followed by a further step, in which the reactivity of peripheral leukocytes, preferably of T-leukocytes, against the isolated antigenic peptides, is tested.

A further object is the method according to the invention, wherein the reactivity of peripheral leukocytes against the isolated antigenic peptides is tested by means of measuring γ-Interferon-mRNA and/or cytokin-mRNA synthesized by the leukocytes.

By detecting γ-Interferon- or cytokin-mRNA it is possible to precisely prove the specific reactivity of leukocytes, preferably of T-lymphocytes against antigenic peptides. Both substances are secreted by activated T-lymphocytes after their activation by corresponding antigenic peptides.

With this additional step candidates of the already identified peptides can be identified even more precisely.

Yet another object is the method according to the invention, wherein, following step (c), a further step is performed, in which the presence of the T-lymphocytes is detected.

Using this method it is possible to specifically detect to what extent T-lymphocytes directed against isolated and identified peptides are pre-existing in patients. By performing this step it is possible to apply, as a vaccine, only those peptides against which T-lymphocytes are already pre-existing in the patient. The peptides can then be used to activate these specific T-lymphocytes.

A further object is the method according to the invention, wherein the detection of specific pre-existing T-lymphocytes is performed by labeling the leukocytes with reconstituted complexes of antigen-presenting molecules and antigenic peptide.

With this method the so-called tetramer-technology is utilized. A method for generating such reconstituted complexes ("tetramers") and for utilizing them is disclosed, for example, in Altman et al., 1996, Phenotypic analysis of antigen-specific T-lymphocytes, Science 274: 94-96.

Further objects of the invention are immunoreactive peptides, which are identified and prepared by the method according to the invention.

After identification these peptides can be selectively and specifically prepared for each patient.

Another object of the invention is a pharmaceutical composition comprising one or more peptides which have been identified and/or prepared by the method according to the invention.

The composition may be applied, for example, parenterally, for example subcutaneously, intradermally or intramuscularly, or may be administered orally. In doing so, the peptides are dissolved or suspended in a pharmaceutically acceptable carrier, preferably an aqueous carrier; the composition can further comprise additives, for example buffers, binders, etc. The peptides can also be administered together with immunostimulating substances, for example cytokines. An extensive description of additives which can be used in compositions of this nature is given, for example, in A. Kibbe, Handbook of Pharmaceutical Excipients, 3. Ed., 2000, American Pharmaceutical Association and Pharmaceutical Press.

According one object of the invention the peptide may be used for treatment of tumor diseases and for preparing a medicament for treatment of tumor diseases.

Tumor diseases to be treated comprise renal, breast, pancreas, gastric, testis and/or skin cancer. Listing of tumor diseases is supposed to be merely illustrative and shall not limit the scope of usage.

The peptide can further be used for assessment of the therapy-course of a tumor disease.

The peptide can also be used for monitoring a therapy in other immunizations or therapies. In that way the peptide according to the invention may not only be used in a therapeutical way but also in a diagnostic way.

A further embodiment object of the invention is using the peptides for generating an antibody.

Polyclonal antibodies can be obtained, in a general manner, by immunization of animals by means of injection of the peptides and subsequent purification of the immunoglobulin.

Monoclonal antibodies can be generated according to standardized protocols, for example as described in Methods Enzymol. (1986), 121, Hybridoma technology and monoclonal antibodies.

Further objects of the invention are nucleic acid molecules coding for the peptide isolated with the method according to the invention.

The nucleic acid molecules can be DNA- or RNA-molecules and can be used for immune therapy of cancer as well.

According to one object of the invention the nucleic acid molecules can be provided in a vector.

A further object of the invention is a cell genetically modified by means of the nucleic acid molecule, such, that the cell is producing a peptide identified according to the invention.

Another object of the invention is a method for preparing an immunoreactive peptide with which a peptide is identified according to the disclosed method and the identified peptide is synthesized chemically, in vitro or in vivo.

Peptides can be prepared by chemical linkage of amino acids, for example by the method of Merrifield, which is known in the art (see Merrifield R B, 1963, J. Am. Chem. Soc. 85:2149-2154).

Peptides can be prepared in vitro, for example, in cell-free systems, and in vivo by using cells.

Another object of the present invention is a method for preparing a vaccine comprising the steps of
 (a) performing the disclosed method,
 (b) preparing the identified immunoreactive peptides, and
 (c) formulating the prepared immunoreactive peptides.

It will be understood that the features which are mentioned above and the features still to be explained below can be used not only in the combinations which are in each case specified but also in other combinations or on their own without departing from the scope of the present invention.

BRIEF DESCRIPTION OF THE DRAWINGS

Embodiments of the invention are displayed and explained in the figures and the example below.

MODES OF CARRYING OUT THE INVENTION

Example 1

Patient Samples

Samples of patients having histologically confirmed renal cell carcinoma were obtained from the department of urology, University of Tubingen. Both patients had not received preoperative therapy. Patient No. 1 (in the following designated RCC01) had the following HLA-typing: HLA-A*02 A68 B*18 B*44; patient No 2 (in the following designated RCCI3) HLA-A*02 A*24 B*07 B*40.

Isolation of MHC Class 1-Bound Peptides

Shock-frozen tumor samples were processed as described in Schirle, M. et al., Identification of tumor-associated MHC-class I ligands by a novel T-cell-independent approach, 2000, European Journal of Immunology, 30: 2216-2225. Peptides were isolated according to standard protocols using monoclonal antibody W6/32 being specific for HLA class I or monoclonal antibody BB7.2 being specific for HLA-A2. Production and utilization of these antibodies is described by Barnstable, C. J. et al., Production of monoclonal antibodies to group A erythrocytes, HLA and other human cell surface antigens—New tools for genetic analysis, 1978, Cell, 14:9-20 and Parham, P. & Brodsky, F. M., Partial purification and some properties of BB7.2. A cytotoxic monoclonal antibody with specificity for HLA-A2 and a variant of HLAA28, 1981, Hum. Immunol., 3: 277-299.

Mass Spectrometry

Peptides from tumor tissue of patient RCCO1 were separated by reversed phase HPLC (SMART-system, μRPC C2/C18 SC 2.1/19, Amersham Pharmacia Biotech) and fractions were analyzed by nanoESI MS. In doing so it was proceeded as described in Schirle, M. et al., Identification of tumor-associated MHC class I ligands by a novel T-cell-independent approach, 2000, European Journal of Immunology, 30: 2216-2225.

Peptides from tumor tissue of patient RCC13 were identified by online capillary LCMS as mentioned above with minor modifications: Sample volumes of about 100 μl were loaded, desalted and preconcentrated on a 300 pm*5 mm C18 μ-precolumn (LC packings). A syringe pump (PHD 2000, Harvard Apparatus, Inc.) equipped with a gastight 100 pμl-syringe (1710 RNR, Hamilton), delivered solvent and sample at 2 μl/min. For peptide separation, the preconcentration column was switched in line with a 75*250 mm C-18-column (LC packings). Subsequently a binary gradient of 25%-60% B within 70 min was performed, applying a 12 μl/min flow rate reduced to approximately 300 nl/min with a precolumn using a TEE-piece (ZT1C, Valco) and a 300 μm*150 mm C-18-column.

A blank run was always included to ensure that the system was free of residual peptides. On-line fragmentation was performed as described and fragment spectra were analyzed manually.

Database searches (NCBInr, EST) were made using MASCOT.

Preparation of RNA

Fragments of normal and malignant renal tissue were dissected, shock-frozen, ground by a mortar and pestle under liquid nitrogen and homogenized with a rotary homogenizer (Heidolph instruments) in TRIZOL (Life Technologies). Total RNA was prepared according to the manufacturer's protocol followed by a clean-up with RNeasy (QIAGEN). Total RNA from human tissues were obtained commercially (Human total RNA Master Panel II, Clontech).

High-Density Oligonucleotide Micro-Array Analysis

Double-stranded DNA was synthesized from 40 μg of total RNA using superscript RT II reverse transcriptase (Life Technologies). The primer (Eurogentec) were given by the Affymetrix manual. In vitro transcription was performed using the BioArray™ High Yield™ RNA Transcript Labeling Kit (ENZO Diagnostics, Inc.); subsequently, fragmentation and hybridization were carried out on Affymetrix HuGeneFL gene chips, and staining with a streptavidin-phycoerythrin and biotinylated anti-streptavidin-antibody followed the manufacturer's protocols (Affymetrix). The Affymetrix GeneArray Scanner was used and data were analyzed with the Microarray Analysis Suite 4.0 Software.

Real Time RT-PCR cDNA generated for microarray analysis was used for quantitative PCR analysis.

Each gene was run in duplicates (40 cycles, 95° C.×15 s, 60° C.×1 min) using SYBRGreen chemistry on the ABI PRISM 7700 sequence detection system (Applied Biosystems). Samples were independently analyzed two to three times. Primers (MWGBiotech) were selected to flank an Intron and PCR efficiencies were tested for all primer pairs and found to be close to 1.

PCR products were analyzed on 3% agarose gels for purity and sequence-verified after cloning into pCR4-TOPO vector using the TOPO TA Cloning Kit (Invitrogen). Data analysis involved the delta CT method for relative quantification.

Laser Capture Microdissection

Embedded frozen tissue specimens were cut at 6 μm thickness and transferred in 70% ethanol for about 15 min. Slides were incubated 90 seconds in Mayer's hematoxylin (Merck), rinsed in water, incubated for 1 min in 70% ethanol, 1 min in 95% ethanol, 30 seconds in 1% alcoholic eosin Y (Sigma), 2×2 min in 95% ethanol, 2×2 min in 100% ethanol and finally 2×2 min in xylene. After air drying for 15 minutes, slides were stored under dry conditions. Normal malignant epithelial tubular cells and carcinoma cells were isolated by a Laser Capture Microdissection (LCM) using the PixCell II LCM system (Arcturus Engineering). Total RNA was extracted in 400 μl TRIZOL.

PBMC, Tetramer Production and Flow Cytometry

Peripheral blood mononuclear cells (in the following PBMC) from two healthy donors (HD1 and HD2), which were serologically typed as CMV-positive, were isolated by gradient centrifugation (FicoLite H) and frozen.

HLA-A *0201 tetrameric complexes were produced as described by Altman et al., 1996, Phenotypic analysis of antigen-specific T-lymphocytes, Science 274: 94-96, as follows: The HLA-A2-binding peptides used for the refolding were ALLNIKVKL (SEQ ID NO: 1) from keratin 18 and NLVPMVATV (SEQ ID NO: 2) from pp65 HCMVA. Tetramers were assembled by mixing biotinylated monomers with streptavidin-PE or streptavidin-APC and 2-3×10⁶ cells were incubated 30 min at 4° C. with both tetramers: 10 μg/ml for each monomer in PBS, 0.01% NaN3, 2 mM EDTA, 50% fetal calf serum). Then, monoclonal antibodies Anti-CD4-FITC (Coulter-Immunotech) and Anti-CD8-PerCP (Becton Dickinson) were added for 20 min. After three washes, samples were fixed in FACS buffer, 1% formaldehyde. Four-color analysis was performed on a FACScalibur cytometer (Becton Dickinson).

Results

The expression of approximately 7,000 genes in tumors and corresponding normal tissue of two renal cell carcinoma was analyzed. Between 400 and 500 genes were found to be overexpressed or selectively expressed in the tumor. 70 genes were overexpressed in the tumors of both patients. In patient I, 268 overexpressed and 129 exclusively expressed genes were found. Most of the overexpressed genes are cancer-related, i.e., either oncogenes, tumor suppressor genes or genes already described as overexpressed in cancer, such as CCND1, CA9, cerebrosidesulfotransferase and parathyroid hormone-like hormone. The cancer-associated adipose differentiation-related protein (ADFP) or adipophilin, showed the second highest degree of overexpression. In addition, this protein was shown to be highly overexpressed in tumorous tissue in comparison to normal tissue of other organs, that is not only in comparison to normal renal tissue.

Figure 1:
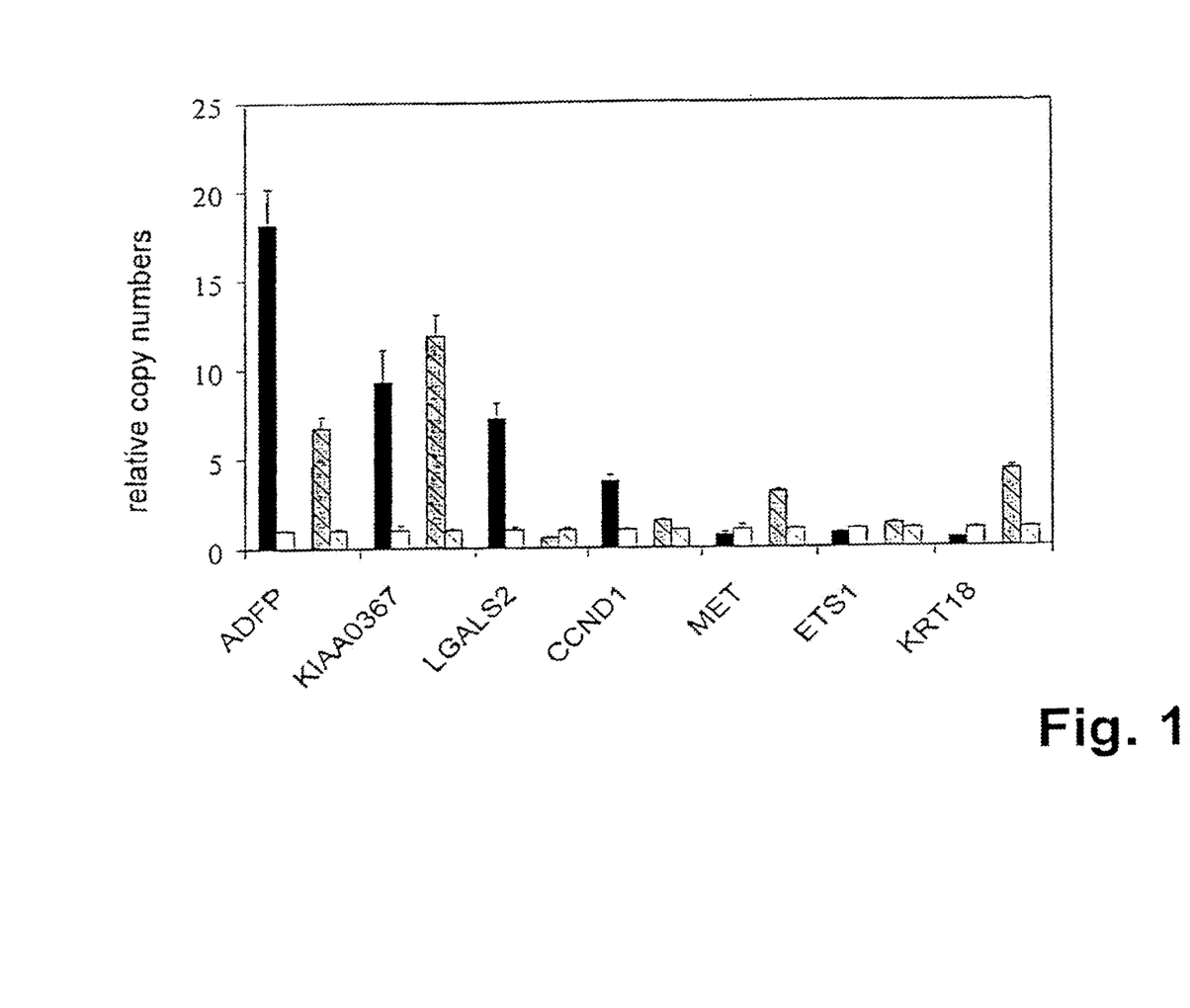
FIG. 1 shows the expression analysis of selected genes by means of quantitative RT-PCR.

To verify data obtained by microarray analysis the expression of selected genes was analyzed by quantitative PCR. In FIG. 1, the expression-analysis of selected genes by means of RT-PCR is shown. The RT-PCR was performed using the same cDNA as generated for microarray analysis. Copy numbers are relative to 18S rRNA and normalized to the normal tissue (=1) of each patient. The black bars correspond to the numbers in tumor tissue of patient RCC01, the white bars represent the numbers of normal tissues and the angular-striped gray bars the numbers in tumor tissue of patient RCC13.

It was shown that overexpression of adipophilin (ADFP) and cycline D1 (CCND1) as proven by microarray could be confirmed by quantitative PCR. Further, it was demonstrated that ets-1 (ETS1) was expressed equally both in normal and in tumor tissue. Further, relative expression levels detected by both techniques were roughly comparable.

For example, adipophilin was overexpressed in tumor tissue of patient RCCOI by a factor of 29.1 as proven by means of microarray, compared to 18.1 as measured by means of quantitative PCR (see FIG. 1). With patient RCC13, by means of microarray analysis a factor of 11.4 and by means of quantitative PCR a factor of 6.7 could be demonstrated (see FIG. 1). Galectin 2 (LGALS2) was overexpressed in patient RCCO1 and keratin-18 (KRT18) in patient RCC13. An exception to the congruence between microarray and quantitative PCR was the overexpression of KIAA0367 and met proto-oncogene (MET) in patient RCC13.

Identification of MHC Class 1-Ligands

A total of 85 ligands could be obtained from tumor tissue, which were bound to HLA-subtypes HLA-A*02, HLA-A*68, HLA-B*18 or HLA-B*44. Peptides that bind to HLAA*02 reflected the allele-specific peptide motif (Leucine, Valine, Isoleucine, Alanine, Methionine on position 2, Leucine, Valine, Isoleucine or Alanine at the C-Terminus). Most ligands were derived from abundantly expressed housekeeping proteins, but ligands from proteins with reported tumor association could be detected also, for example, YVDPVITSI (SEQ ID NO: 3) derived from met proto-oncogene, ALLNIKVKL (SEQ ID NO: 1) derived from keratin 18, and SVASTITGV (SEQ ID NO: 4) from adipophilin.

HLA-A*68 ligands were identified by their anchor amino acids Threonine, Isoleucine, Valine, Alanine or Leucine on position 2 and arginine or lysine at the C-terminus. Two other ligands from adipophilin were found among HLA-A*68-presented peptides: MTSALPIIQK (SEQ IDS NO: 5) and MAGDIYSVFR (SEQ ID NO: 6). Ligands carrying glutamic acid on position 2 were assigned to HLA-B*44; since the peptide motif of HLA-B*18 is unknown, a distinction between ligands of these two HLA-B-molecules was not possible.

Comparison of microarray data with the isolated ligands indicated 10 overexpressed genes as sources for MHC-ligands: adipophilin, KIAA0367, SEC14-like 1, B-cell translocation gene 1, aldolase A, cycline D1, annexin A4, catenin alpha 1, galectin 2 and LMP2. Three of them were also included in the SEREX database: KIAA0367, aldolase A and catenin alpha 1.

A most interesting ligand could be identified from patient RCC13 (ALAAVVTEV SEQ ID NO: 7)) encoded by a "Reading frame" shifted by one nucleotide compared to DEAD/H-box polypeptide 3 (DDX3). ALAAVVTEV (SEQ IF NO: 7) is encoded by the nucleotides 317 to 343 of the coding strand of DDX3, whereas nucleotides 316 to 342 are coding for GIGSRGDRS (SEQ ID NO: 8) of the DDX3 protein.

Detection of Specific T-ceHs in Normal CD8+ T-Cell Repertoire

PBMC from 6 HLA-A2 positive renal cell carcinoma patients were tested for reaction against four of the relevant peptides: HLA-A*02-restricted ligands from adipophilin, keratin 18, K1AA0367 and met-proto-oncogene. In doing so, a very sensitive quantitative PCT assay was carried out to detect γ-Interferon-mRNA production by CD8+ T-cells following a 7 day-in vitro-sensitization with peptide. Sporadic responses were seen after stimulation with met-proto-oncogene or keratin 18 or adipophilin peptides.

Staining of PBMC of tumor patients and healthy individuals with HLA-A*0201 tetramers was performed with tetramers reconstituted either with adipophilin, keratin 18 or met-proto-oncogene.

Figure 2:
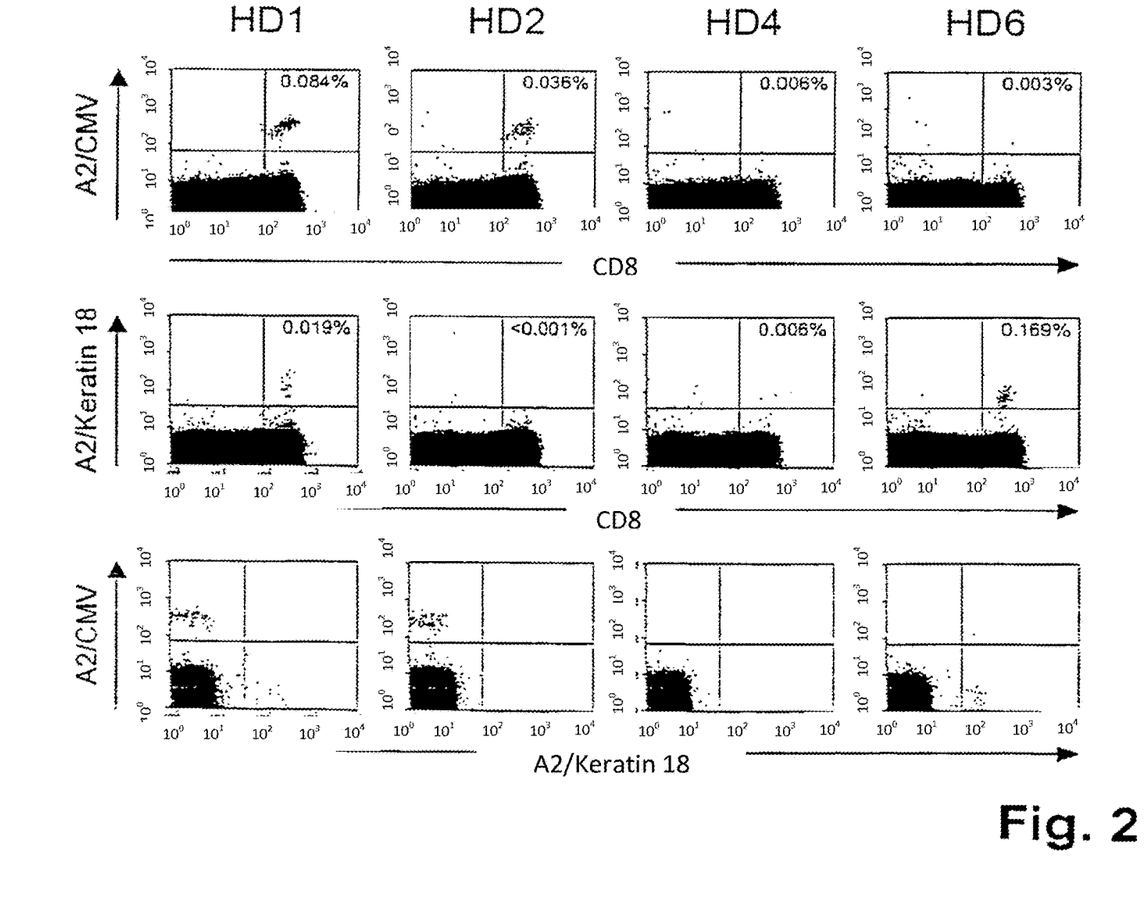
FIG. 2 shows the detection of keratin 18-specific CD8+ T-lymphocytes.

FIG. 2 shows the detection of keratin 18-specific T-lymphocytes. For this purpose, PBMC from four healthy HLA-A*02+ donors (HD 1, 2, 4, 6) were simultaneously stained with HLA-A2/keratin 18-PE tetramers, HLA-A2/CMV-APC tetramers, CD8-PerCP and CD4-FITC. Dot plots show samples from one of three independent experiments for 1×10$^6$ PBMC. In the plots, percentage of tetramer+-cells within the CD8+ CD4− population are indicated.

Unexpectedly, a significant population of CD8+ T-lymphocytes specific for keratin 18 (between 0.02% and 0.2% of CD8+ T-cells) was found in 4 out of 22 healthy individuals. This population did not stain with a CMV tetramer showing that the binding of keratin 18 tetramer was specific.

To summarize, it can be concluded that CD8+ T-lymphocytes specific for the keratin 18-peptide are contained in the human T-cell repertoire.

What is claimed is:

1. A method for identifying antigenic peptides for use to induce a CTL immune response in an individual comprising:
   a) determining HLA-subtypes of the individual,
   b) obtaining a tumor sample and a corresponding healthy tissue sample from the individual,
   c) identifying one or more genes that are overexpressed in the tumor sample relative to the healthy tissue sample using microarray analysis or RT-PCR,
   d) identifying one or more antigenic peptides bound to the HLA-subtypes in the tumor sample by mass spectrometry,
   e) selecting only the antigenic peptides from step d), which are encoded by an overexpressed gene from step c), wherein the antigenic peptides are selected from the group consisting of ALLNIKVKL (SEQ ID NO: 1), YVDPVITSI (SEQ ID NO: 3), SVASTITGV (SEQ ID NO: 4), MTSALPIIQK (SEQ ID NO: 5), MAGDIYSVFR (SEQ ID NO: 6), ALAAVVTEV (SEQ ID NO: 7), and GIGSRGDRS (SEQ ID NO: 8), and
   f) synthesizing said antigenic peptides selected in step e), wherein the CTL immune response is induced in the individual.

2. The method of claim 1, wherein the antigenic peptides selected in step e) are patient-specific.

3. The method of claim 1, wherein the antigenic peptides selected in step e) are generated by a reading-frame shift mutation.

4. The method of claim 1, wherein after step e) a further step is performed, wherein the reactivity of T-lymphocytes is tested against the antigenic peptides selected in step e).

5. The method of claim 2, wherein after step e) a further step is performed, wherein the reactivity of T-lymphocytes is tested against the antigenic peptides selected in step e).

6. The method of claim 3, wherein after step e) a further step is performed, wherein the reactivity of T-lymphocytes is tested against the antigenic peptides selected in step e).

7. The method of claim 4, wherein the reactivity test is performed by means of measuring cytokine-mRNA and/or gamma-Interferon mRNA synthesized by the T-lymphocytes.

8. The method of claim 5, wherein the reactivity test is performed by means of measuring cytokine-mRNA and/or gamma-Interferon mRNA synthesized by the T-lymphocytes.

9. The method of claim 6, wherein the reactivity test is performed by means of measuring cytokine-mRNA and/or gamma-Interferon mRNA synthesized by the T-lymphocytes.

10. The method of claim 1, further comprising calibrating the mass spectrometer based on candidate antigenic peptides predicted by an expression profile in a database.

11. The method of claim 1, further comprising detecting a T cell in the individual.

12. The method of claim 11, wherein the detecting comprises labelling the T cell with a complex comprising the antigenic peptides selected in step e), the HLA-subtypes, and a streptavidin-conjugated with a probe.

13. The method of claim 12, wherein the complex is a tetramer.

14. The method of claim 13, wherein the tetramer is prepared by biotinylating the HLA-subtypes and mixing the biotinylated HLA-subtypes bound with the antigenic peptides selected in step e) with the conjugated streptavidin.

15. The method of claim 14, wherein the conjugated streptavidin is streptavidin-phycoerythrin (PE) or streptavidin-allophycocyanin (APC).

16. The method of claim 15, wherein the detecting further comprises staining a peripheral blood mononuclear cell (PBMC) from the individual using the tetramer.

17. The method of claim 11, wherein the T cell is a CD8$^+$ T cell.

18. The method of claim 1, further comprising formulating the synthesized antigenic peptides for administering to the individual.

19. The method of claim 1, further comprising isolating the one or more antigenic peptides identified in step d).

20. The method of claim 19, wherein the isolating comprises binding the one or more antigenic peptides bound to the HLA-subtypes with an anti-HLA-subtypes antibody.

21. The method of claim 20, wherein the anti-HLA-subtypes antibody is a monoclonal antibody W6/32 specific for HLA class I or a monoclonal antibody BB7.2 specific for HLA-A2.

22. The method of claim 21, wherein the isolating further comprising separating the one or more antigenic peptides by reversed phase HPLC.

23. The method of claim 1, wherein the tumor sample and the corresponding healthy tissue sample are embedded frozen tissues.

24. The method of claim 1, wherein the one or more genes identified by the microarray analysis is verified by the RT-PCR.

25. The method of claim 1, wherein the HLA-subtypes comprises HLA-A*02, HLA-A*68, HLA-B*18, and HLA-B*44.

26. The method for identifying antigenic peptides for use to induce a CTL immune response in an individual of claim 1, consisting of:

a) determining HLA-subtypes of the individual, b) obtaining a tumor sample and a corresponding healthy tissue sample from the individual, c) identifying one or more genes that are overexpressed in the tumor sample relative to the healthy tissue sample using microarray analysis or RT-PCR, d) identifying one or more antigenic peptides bound to the HLA-subtypes in the tumor sample by mass spectrometry, e) selecting only the antigenic peptides from step d), which are encoded by an overexpressed gene from step c), wherein the antigenic peptides are selected from the group consisting of ALLNIKVKL (SEQ ID NO: 1), YVDPVITSI (SEQ ID NO: 3), SVASTITGV (SEQ ID NO:4), MTSALPIIQK (SEQ ID NO: 5), MAGDIYSVFR (SEQ ID NO: 6), ALAAVVTEV (SEQ ID NO: 7), and GIGSRGDRS (SEQ ID NO: 8), and f) synthesizing said antigenic peptides selected in step e), wherein the CTL immune response is induced in the individual.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Ala Leu Leu Asn Ile Lys Val Lys Leu
1               5

<210> SEQ ID NO 2
<211> LENGTH: 9
<212> TYPE: PRT
<213> ORGANISM: Homo sapiens

<400> SEQUENCE: 2

Asn Leu Val Pro Met Val Ala Thr Val
1               5

<210> SEQ ID NO 3
<211> LENGTH: 9
<212> TYPE: PRT
<213> ORGANISM: Homo sapiens

<400> SEQUENCE: 3

Tyr Val Asp Pro Val Ile Thr Ser Ile
1               5

<210> SEQ ID NO 4
<211> LENGTH: 9
<212> TYPE: PRT
<213> ORGANISM: Homo sapiens

<400> SEQUENCE: 4

Ser Val Ala Ser Thr Ile Thr Gly Val
1               5

<210> SEQ ID NO 5
<211> LENGTH: 10
<212> TYPE: PRT
<213> ORGANISM: Homo sapiens

<400> SEQUENCE: 5

Met Thr Ser Ala Leu Pro Ile Ile Gln Lys
1               5                  10
```

-continued

```
<210> SEQ ID NO 6
<211> LENGTH: 10
<212> TYPE: PRT
<213> ORGANISM: Homo sapiens

<400> SEQUENCE: 6

Met Ala Gly Asp Ile Tyr Ser Val Phe Arg
1               5                   10

<210> SEQ ID NO 7
<211> LENGTH: 9
<212> TYPE: PRT
<213> ORGANISM: Homo sapiens

<400> SEQUENCE: 7

Ala Leu Ala Ala Val Val Thr Glu Val
1               5

<210> SEQ ID NO 8
<211> LENGTH: 9
<212> TYPE: PRT
<213> ORGANISM: Homo sapiens

<400> SEQUENCE: 8

Gly Ile Gly Ser Arg Gly Asp Arg Ser
1               5
```